(12) United States Patent
Van Dun et al.

(10) Patent No.: US 6,603,064 B1
(45) Date of Patent: Aug. 5, 2003

(54) NUCLEAR MALE STERILE PLANTS, METHOD OF PRODUCING SAME AND METHODS TO RESTORE FERTILITY

(75) Inventors: Cornelis Maria Petrus Van Dun, Roosendaal (NL); Oscar Johannes Maria Goddijn, Leiden (NL)

(73) Assignee: Syngenta Mogen B.V., Leiden (NL)

( * ) Notice: Subject to any disclaimer, the term of this patent is extended or adjusted under 35 U.S.C. 154(b) by 0 days.

(21) Appl. No.: 09/530,072

(22) PCT Filed: Oct. 30, 1998

(86) PCT No.: PCT/EP98/07008
§ 371 (c)(1),
(2), (4) Date: Jul. 21, 2000

(87) PCT Pub. No.: WO99/23233
PCT Pub. Date: May 14, 1999

(30) Foreign Application Priority Data

Oct. 30, 1997 (EP) .............................. 97203373

(51) Int. Cl.$^7$ ................ C12N 15/82; C12N 15/84; C12N 15/31; A01H 1/02; A01H 5/00
(52) U.S. Cl. .............. 800/303; 800/271; 800/274; 800/278; 800/284; 800/287; 800/288; 800/294; 800/300; 435/194; 435/252.2; 435/252.3; 435/320.1; 435/468; 435/469
(58) Field of Search ................ 800/271, 274, 800/278, 284, 287, 288, 294, 303, 300; 435/252.2, 252.3, 320.1, 468, 469, 194

(56) References Cited

FOREIGN PATENT DOCUMENTS

| EP | 0 784 095 A2 | 7/1997 |
|---|---|---|
| WO | WO 93/03616 | 3/1993 |
| WO | WO 96/00789 | 1/1996 |
| WO | WO 97/10703 | 3/1997 |
| WO | WO 97/13401 | 4/1997 |
| WO | WO 97/30581 | 8/1997 |
| WO | WO 97/42326 | * 11/1997 |

OTHER PUBLICATIONS

Vogel et al. Plant J. 13(5): 673–683, 1998.*
Pilon–Smits et al. J. Plant Physiol. 152:525–532, 1998.*
Goodijn, O.J.M. et al., Plant Physiology, vol. 113, No. 1 Jan. 1997, pps. 181–190.
Veluthambi K. et al., Plant Physiology, vol. 68, Jan. 1, 1981, pps. 1369–1374.
Zentella R. et al., Plant Physiology, vol. 111, No. 2, Jun. 1996, pp. 47.
Kasembe, J.N.R., Nature, vol. 215, 1967, pp. 668.

* cited by examiner

Primary Examiner—David T. Fox
(74) Attorney, Agent, or Firm—Edouard G. Lebel

(57) ABSTRACT

The present invention is directed to the production of male sterile plants by providing them with a recombinant DNA capable of specific expression in the male reproductive system of a plant of the enzyme trehalose phosphate (TPP). Resotration of the fertility can be established either by providing said male sterile plants with a recombinant DNA capable of expression of trehalose phosphate synthase (TPS) under control of an inducible promoter or with a recombinant DNA capable of expression of a suppressor protein which suppresses expression of TPP under control of an inducible promoter. This inducible restoration possibilities enable the maintenance of a homozygous male sterile line. Restoration can also be done by spraying the male sterile plants with gibberellic acid. For production of hybrids or hybrid seed a site-specific recombination system is provided, by inserting two site=specific recombination sites flanking the recombinant DNA coding for TPP and crossing the male sterile lines with lines expressing the corresponding recombinase. By crossing the recombinase will excise the gene coding for TPP and fertile hybrids are produced.

14 Claims, 9 Drawing Sheets

Fig.8 Restoration of fertility of Tap-TPP tobacco after re-transformation with Tap-TPS

Restoration of fertility of Tap-TPP tobacco by Gibberelic Acid treatment
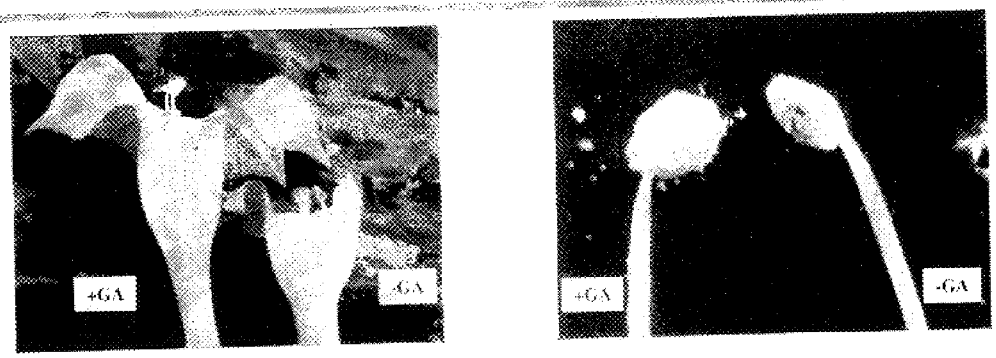
Fig.9
ZENECA *MO<sub>GEN</sub>*

NUCLEAR MALE STERILE PLANTS, METHOD OF PRODUCING SAME AND METHODS TO RESTORE FERTILITY

RELATED APPLICATIONS

Pursuant to 35 U.S.C. § 371, this application claims priority to PCT/EP98/07008, filed Oct. 30, 1998.

FIELD OF THE INVENTION

This application concerns conferring nuclear male sterility to plants by transforming them with recombinant DNA and methods to restore fertility in these male sterile lines.

BACKGROUND ART

It has since long been acknowledged that seeds derived through cross-pollination between different parental lines of one species, give rise to offspring with better characteristics in terms of yield, uniformity, environmental fitness, and disease resistance, when compared with the offspring of seeds derived through self-pollination. This effect is generally referred to as the heterosis effect. For this reason it is an object for the seed industry to obtain hybrid seed in as many agricultural and horticultural crops as possible, because of their higher commercial value.

The development of hybrid cultivars of various plant species depends upon the capability of achieving almost complete crosspollination between parents. This is most simply achieved by rendering one of the parent lines male sterile (i.e. bringing them in a condition so that pollen is absent or nonfunctional) either manually, by removing the anthers, chemically or genetically by using, in the one parent, cytoplasmatic or nuclear genes that prevent anther and/or pollen development.

For hybrid plants where the seed is the harvested product (e.g. corn, wheat, oilseed rape) it is also necessary to ensure that fertility of the hybrid plants is restored. In systems in which the male sterility is under genetic control this requires the existence and use of genes that can restore male fertility. The development of hybrid cultivars by genetic modification is dependent on the availability of suitable and effective sterility and restorer genes.

Another goal of making plants male sterile is in protection of the (parent line) germplasm and prevention of breeding with farm-saved seeds and/or plants. If it is possible to create seeds resulting in homozygous sterile plants, it is impossible to obtain seed from them and to breed these further. Thus, a monopoly position for the distribution of these seeds or plants can be maintained. This is especially important for crops such as cauliflower, grasses, etc., in which the reproductive organs (as e.g. seed) are not the commercial target for the farmer. However, in order to propagate male sterile homozygous parent lines, the fertility should be restorable to obtain viable pollen.

Endogenous nuclear loci are known for most plant species that may contain genes which effect male fertility, and generally, such loci need to be homozygous for particular recessive alleles in order to result in a male-sterile phenotype. The presence of a dominant 'male fertile' allele at such loci results in male fertility.

In the last ten years it has been shown that a dominant male sterility trait can be induced in a plant by providing the genome of the plant with a recombinant DNA sequence coding, for example, for a cytotoxic product and under the control of a promoter which is predominantly active in selected tissue of the male reproductive organs.

In the prior art already a number of DNA sequences inducing male sterility and specific promoters have been elucidated.

In the International Patent Application WO 90/08830, ICI proposes methods for the production of restorable male-sterile plants in general terms, essentially comprising expression of a) either a gene encoding a protein inhibitor, or b) a so-called killer gene, which said genes are to be expressed in the male flowers, leading to cell death of the anthers and associated tissues. Exemplified killer genes are those which upon expression have an effect on mitochondrial metabolism.

In the International Patent Application WO 90/08831, ICI discloses the inhibition of cell-respiration and mitochondrial function by expression of a disrupter gene, eventually resulting in the death of the cells in which these genes are expressed. Preferred disrupter proteins are (a) the mammalian uncoupling protein (UCP); (b) a mutated form of the gene for the β-1 subunit of FI-ATPase, such that the changes result in the disability of the subunits to assemble into a functional ATP-synthase; (c) a mutated, synthetic form of the oli I gene encoding subunit 9 of the OF-ATPase; (d) mutated forms of a mitochondrial transit peptide in order to disrupt protein transport to mitochondria; and (e) gene-constructs involving a fusion between the β-subunit (ATPase) gene from yeast and the P-galactosidase gene from *E. coli*, resulting in expression of a disrupting fusion protein. Preferably such expression, according to the specification, should be regulated under the control of a tapetum- or pollen-specific promoter.

In the International Patent Application WO 89/10396, PGS proposes methods in general terms for obtaining male-sterile plants, by transforming the nuclear genome of the plant with a so-called "male-sterility DNA." The "male-sterility DNA" comprises DNA that encodes an RNA or polypeptide capable of disturbing the proper metabolism, functioning, and/or development of any stamen cell in which it is expressed, preferably leading thereby to the death of any such stamen cell. Examples of such "male-sterility DNAs" are those encoding DNAses, RNAses, proteases, or enzymes of phytohormone synthesis, such as cytokinin. Alternatively, it is proposed to select "male-sterility DNAs" from antisense DNAs, "which encode a strand of DNA complementary to a strand of DNA that is naturally transcribed in the plant's stamen cells."

In the European Patent Application EP-A-0 329 308, Palladin Hybrids proposes a method to provide male-sterile plants, comprising producing a genetically transformed female parent, by essentially inserting into the genome of the said plant recombinant DNA sequences comprising anti-sense DNA, which blocks the production of functional pollen grains or renders the developing pollen grains susceptible to a chemical agent or physiological stress that blocks the production of functional pollen grains. Preferably, said antisense genes are expressed under the control of a pollen- specific promoter. Genes which are critical to production of functional pollen grains, according to the specification of EP-A-0 329 308, are to be selected from genes that are specifically expressed in the microspores, preferably in the premeiotic stage. Examples of microspore specific clones are LA and L19, derived from *Brassica napus*. Apart from the general indication to premeiotic genes and the expressly mentioned clones, no further teachings are given with respect to the nature of the genes the expression of which is to be blocked.

Also compounds of the flavonoid pathways have been used. EP 0 513 884 (MOGEN) is directed to the anther-specific disruption of the chalcone synthase pathway. Similarly, disruption of the anthocyanin biosynthesis in the seeds has been proposed (WO 95/34634, PGS).

Restoration of fertility has also been described. WO 94/09143 (MOGEN) mentions a restoration system for the anther-specific disruption of the chalcone synthase pathway. A sterility-fertility system has been provided in EP 0 628 635 (NUNHEMS), where sterility is caused by locally creating defects in amino acid biosynthesis pathways, while restoration is envisaged by supplying the missing amino acid or precursors through watering or spraying. WO 89/10396 (PGS) proposed to restore the fertility in plants made sterile by expression of the RNAse barnase by introducing a gene encoding barstar, the specific inhibitor of barnase.

Restoration by excising the gene responsible for the sterility through site-specific recombination by crossing a sterile plant with a plant expressing a recombinase has been disclosed in WO 97/13401 (Purdue Res. Found.).

However, there is still a need for a system that confers complete male sterility and is equally well subject to restoration.

SUMMARY OF THE INVENTION

This invention is directed to a method to make a plant male sterile by transforming it with a recombinant DNA capable of expression of a protein in the tapetum, pollen and/or anthers, characterized in that the protein is trehalose phosphate phosphatase (TPP). Said recombinant DNA comprising the gene coding for TPP is of bacterial, fungal, animal, plant or human origin, preferably derived from *Escherichia coli*.

Also part of the invention is a recombinant DNA comprising a tapetum, pollen and/or anther specific promoter and a gene coding for TPP, preferably a gene of bacterial, fungal, animal, plant or human origin, more preferably derived from *Escherichia coli*. Furthermore, vectors comprising this recombinant DNA and Agrobacterium strains comprising this vector form part of the invention. Equally plants transformed with this Agrobacterium strain or, in general, plants comprising the above-described recombinant DNA or plants made according to the above-described method form part of the invention.

Another embodiment of the invention is a method for making a plant male sterile and susceptible to restoration of male fertility by transforming a plant with recombinant DNA encoding TPP and which coding sequence is flanked by target sites of a site-specific recombinase. The accompanying method for restoration of fertility in a male sterile plant made according to this method is characterized in that the recombinant DNA encoding TPP is removed by providing said plant, either through transformation or through crossing, with a recombinant DNA capable of expressing a site-specific recombinase.

Also an embodiment of the invention is a method for making a plant male sterile and susceptible to restoration of male fertility by transforming it with a recombinant DNA capable of expression in the tapetum, pollen and/or anthers, characterized in that the recombinant DNA comprises a gene coding for trehalose phosphate phosphatase (TPP) and a gene coding for trehalose phosphate synthase (TPS) or other genes which inhibit the effect of TPP, such as antisense trehalase or antisense TPP, which last genes are under control of an inducible promoter. The accompanying method for restoration of fertility in a male sterile plant made according to this method is characterized in that TPS is expressed by induction of the inducible promoter.

A further embodiment of this invention is found in a method for making a plant male sterile and susceptible to restoration of male fertility by transforming it with a recombinant DNA capable of expression in the tapetum, pollen and/or anthers, characterized in that the recombinant DNA comprises a gene coding for trehalose phosphate phosphatase (TPP) of which the expression is controlled by a suppressor molecule encoded by a gene which is controlled by an inducible promoter. The accompanying method for restoration of fertility in a male sterile plant made according to this method is characterized in that the suppressor is expressed by induction of the inducible promoter.

A further embodiment of the invention is a method of restoration of plants made male sterile by the expression of trehalose phosphate phosphatase by applying a solution of gibberellic acid to said plants and more especially to the flower buds.

Other embodiments of this invention are male sterile plants produced by the above-described methods and the corresponding male fertility-restored plants produced by the accompanying fertility restoration methods.

Also included in this invention are methods for producing a male sterile homozygous line by crossing a male sterile plant as obtained according to the methods of the invention with a restored male fertile plant also obtained through the methods of the invention. Also the male sterile homozygous line produced by this method forms part of the invention.

A final embodiment of the invention is a method for the production of fertile hybrid plants by a. transforming a plant with a recombinant DNA capable of expressing a site-specific recombinase; and b. crossing said plant with a male sterile plant produced by any of the above described methods.

Also, the fertile hybrid plants produced by this method are part of the invention.

BRIEF DESCRIPTION OF THE FIGURES

FIG. 9 Restoration of fertility of tap-TPP tobacco Samsun NN plants by treatment with gibberellic acid (GA). Upper left panel shows development of corona and pollen development on the anthers, upper right panel shows detail of pollen development on anthers, bottom panel shows seed setting.

DETAILED DESCRIPTION OF THE INVENTION

Figure 1:
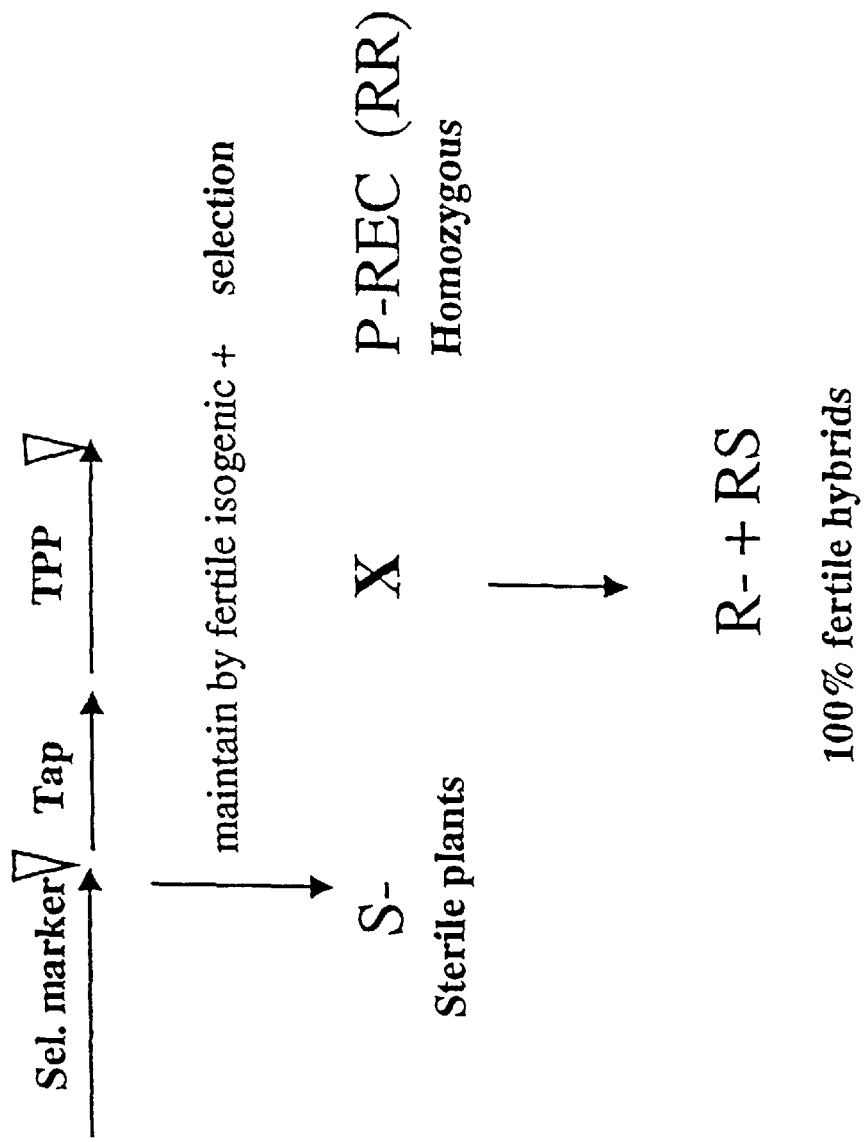
FIG. 1 Flow scheme of the production of fertile hybrids in a nuclear male sterility system based on the expression of TPP and sitespecific recombination.

Provided are methods for making male sterile plants, the male sterile plants themselves, methods to restore fertility in said plants, the restored fertile plants, and methods of making fertile hybrids.

Male sterility is the failure or inability to produce functional or viable pollen. Male sterility may result from defects leading to the non- formation of pollen or to the lack of functional ability in the pollen when it is formed. Therefore, either pollen is not formed or, if formed, it is either non-viable or incapable of effective fertilisation under normal conditions.

The male sterile plants of the invention are female fertile. This means that the plants do not produce fertile pollen, yet are capable of accepting pollen from the desired paternal parent resulting in fertilisation and seed production.

For definition purposes only the general term of a transformed cover a broad spectrum of plants and plant species and is not confined to one specific variety.

The basis of this invention is found in the fact that it has been surprisingly found that expression of TPP, specifically in the male reproductive tissues such as the tapetum layer, the anthers or in pollen, gives male sterility. TPP is an enzyme which is active in the trehalose synthesis pathway, which is not known to be present in reproductive tissue. However, it has been recently found (WO 97/42326) that the enzymes TPS and TPP are able to change dramatically the carbohydrate metabolic and photosynthetic capacity of tissues in which they are expressed. It has furthermore been found that the effects of TPP and TPS are opposite, i.e. by simultaneous equimolar expression no major effects on the plant physiology and phenotype will be observed. It is also envisaged that other enzymes involved in the trehalose biochemical pathway, such as trehalase, trehalose-6-phosphate hydrolase TreC (Rimmele, M. and Boos, W., J. Bact. 176, 5654–5664, 1994), and phospho-alpha-(1,1)-glucosidase (Schoeck, F. et al., Gene 170, 77–80, 1996) can be used to produce the effects as described in this application.

Generally, male sterile plants are obtained by the expression of TPP under control of a promoter which specifically drives expression in the male reproductive system of a plant. Promoters that show this specificity are well known. Especially useful are the tapetum-specific promoter Tap1 as described in Nacken et al. Sol. Gen. Genet. 229, 129–136, 1991), the tapetum specific promoter A9 (WO 92/11379), the anther specific promoters described in WO 92/18625, WO 90/08826 and European patent application EP 93810455.1, and the tapetum specific promoter MFS14 (WO 97/04116). Several other promoters are known in the art (see, e.g., McCormick et al. "Anther-Specific Genes: Molecular Characterization and Promoter Analysis in Transgenic Plants" in Plant Reproduction: From Floral Induction to Pollination, Lord et al. (ed.), 128–135, 1989; and Scott et al., 1992, The Plant Cell 4, 253) and as long as they give specific expression in the male reproductive system, choice of the promoter is not critical to the invention.

It must, however, be kept in mind that the effect of anther- or tapetum-specific expression differs from the effect of pollen-specific expression. When using anther- or tapetum-specific expression of a gene that inhibits the formation of viable pollen, no pollen at all is formed. Such a plant is effectively male sterile. Upon pollen-specific expression, however, half of the pollen is viable, while the other half is not. Thus, this heterozygous plant is still fertile (but for 50%). To obtain a truly homozygous sterile line with a pollen-specific promoter, the sterility conferring gene should be under the control of an inducible promoter, so that, at first, when the gene is not yet expressed, plants can be made which are homozygous for said inducible gene. After induction, the gene will be expressed, and the plant becomes male sterile. This system thus enables the maintenance of a line which can be made male sterile at any moment. It must be clear that inducible sterility is a property that can be obtained with any male reproductive system specific promoter if joined with an inducible promoter.

The TPP gene encodes a trehalose phosphate phosphatase. Several genes coding for this enzyme are known and can be found in all kinds of organisms (PCT/EP 97/02497). In the experiments sustaining the invention, the gene derived from Escherichia coli is used, but also other genes coding for TPP, e.g. those derived from yeast or plants, are equally useful. In other embodiments of the invention, the trehalose phosphate synthase gene (TPS) is used. Also, this gene is derived from *E. coli*, but it can equally well be derived from other organisms such as yeast, plants, or even humans (WO 97/42326).

It may be kept in mind that it has been shown in WO 97/42326 that expression of TPP under control of a less specific promoter can also yield male-sterile plants. Such has been demonstrated in tobacco with expression of TPP under control of a 35S promoter and under control of a plastocyanin promoter and in Arabidopsis with expression of TPP under control of the plastocyanin promoter (WO 97/42326, Example 2 and Example 20, respectively).

A number of different site-specific recombinase systems can be utilized in accordance with the present invention, including but not limited to the Cre/lox system of bacteriophage PI, the FLP/FRT system of yeast, the Gine recombinase of phage Mu, the Pin recombinase of *E. coli*, and the R/RS system of the pSR1 plasmid. The two most used site-specific recombinase systems are the bacteriophage P1 cre/lox and the yeast FLP/FRT systems. In these systems a recombinase (Cre or FLP) interacts specifically with its respective site-specific recombination sequence (lox or FRT, respectively) to invert or excise the intervening sequences. The sequence for each of those two systems is relatively short (34 by for lox and 34-47 by for FRT). Use of such a site-specific recombinase in plants is, for example, described in U.S. Pat. No. 5,527,695. The DNA to be excised can be flanked by direct repeats of the site-specific recombination site, and subsequent introduction of the recombinase activity excises the DNA (and thus restores fertility). The FLP/FRT recombinase system has been demonstrated to function efficiently in plant cells. Although the site-specific recombination sequences must be linked to the ends of the DNA sequence to be excised or inverted, the gene encoding the site-specific recombinase may be located elsewhere and thus can be separately introduced into the plant cells through standard transformation procedures, or through cross-pollination with a plant that already contains the recombinase gene.

In its simplest form (see FIG. 1), the invention is directed to producing fertile hybrids by crossing a male sterile line, generated by introducing a recombinant DNA having a selectable marker (for instance herbicide resistance) and capable of expressing the TPP specifically in the male reproductive system, and a line expressing a gene that can neutralize the sterility inducing effect of the TPP. Such fertile hybrids may be produced by crossing the male sterile line with plants that express trehalose phosphate synthase (TPS), plants that express the anti-sense TPP gene, plants that express a suppressor which is capable of inhibiting expression of the TPP, and plants making use of a site-directed recombination system. The invention is not limited to these methods, and a person skilled in the art will recognize that there are several ways to prevent expression (at the transcriptional, translational, or post-translational level) or functioning of the TPP gene.

The male sterile line (because it is still heterozygous) can be maintained by fertile isogenic treatment (crossing with a nontransgenic, i.e. fertile line) and selection. Selection is done with the agent for which the transgenic line has been made resistant, for instance antibiotics like kanamycin and hygromycin, or herbicides like Basta and glyphosate. The choice of a suitable marker is well within the scope of the averaged skilled worker; some examples of routinely used marker genes are the neomycin phosphotransferase genes conferring resistance to kanamycin (EP-A 256 223), the glutathion-S-ransferase gene from rat liver conferring resistance to glutathione derived herbicides (EP-A 256 223), glutamine synthetase conferring upon overexpression resistance to glutamine synthetase inhibitors such as phosphinotrycin (WO 87/05327), the acetyl transferase gene from Streptomyces viridochromogenes conferring resistance to the selective agent phosphinotrycin (EP-A 275 957), the gene encoding a 5-enolshikimate-3-phosphatase synthase (EPSPS) conferring tolerance to N-phosphomethylglycine, the hpt gene which confers hygromycin resistance and the cah gene which gives resistance to cyanamid, the bar gene conferring resistance to Bialaphos (e.g. WO 91/02071) and the like. The actual choice of the marker is not crucial as long as it is functional (i.e. selective) in combination with the plants of choice.

However, mostly a homozygous male sterile line is preferred. This poses problems for the maintenance of such a line. This has been solved in this invention in several ways.

If the goal is to provide a homozygous male sterile line, the effects of TPP in the male sterile lines should be overcome in order for them to successfully cross. This can be done in several ways, only some of which will be explicitly mentioned here. The invention is not limited to these examples; a person skilled in the art can easily find other ways of achieving the same goal.

A first means of restoring fertility is the introduction of a gene encoding a molecule counteracting the effect of TPP next to the TPP gene. An example of such a gene is TPS, which is able to overcome the sterility effects caused by TPP. To prevent the constitutive expression of TPS, it is envisaged to bring expression of TPS under control of an inducible promoter. Inducible promoters include any promoter capable of increasing the amount of gene product produced by a given gene in response to exposure to an inducer. In the absence of an inducer, the DNA sequence will not be transcribed. Typically, the factor that binds specifically to an inducible promoter to activate transcription is present in an inactive form, which is then directly or indirectly converted to the active form by the inducer. The inducer may be a chemical agent, such as a protein, metabolite (sugar, alcohol, etc.), a growth regulator, herbicide, a phenolic compound, or a physiological stress imposed directly by heat, salt, wounding, toxic elements, etc. or indirectly through the action of a pathogen or disease agent such as a virus. A plant cell containing an inducible promoter may be exposed to an inducer by external application of the inducer to the cell, such as by spraying, watering, heating, or similar methods. Inducible promoters are known to those familiar with the art, and several exist that could conceivably be used to drive expression of the TPS gene. Inducible promoters suitable for use in accordance with the present invention include, but are not limited to, the heat shock promoter, the mammalian steroid receptor system, and any chemically inducible promoter. Examples of inducible promoters include the inducible 70 kD heat shock promoter of *Drosophila melanogaster* (Freeling, M. et al., Ann. Rev. Genet. 19, 297–323) and the alcohol dehydrogenase promoter, which is induced by ethanol (Nagao, R. T. et al., in Miflin, B. J. (ed.) Oxford Univ. Press, 1986). A promoter that is inducible by a simple chemical is particularly useful. Examples of the last category are the promoters described in WO 90/08826, WO 93/21334, WO 93/031294, and WO 96/37609.

Figure 2:
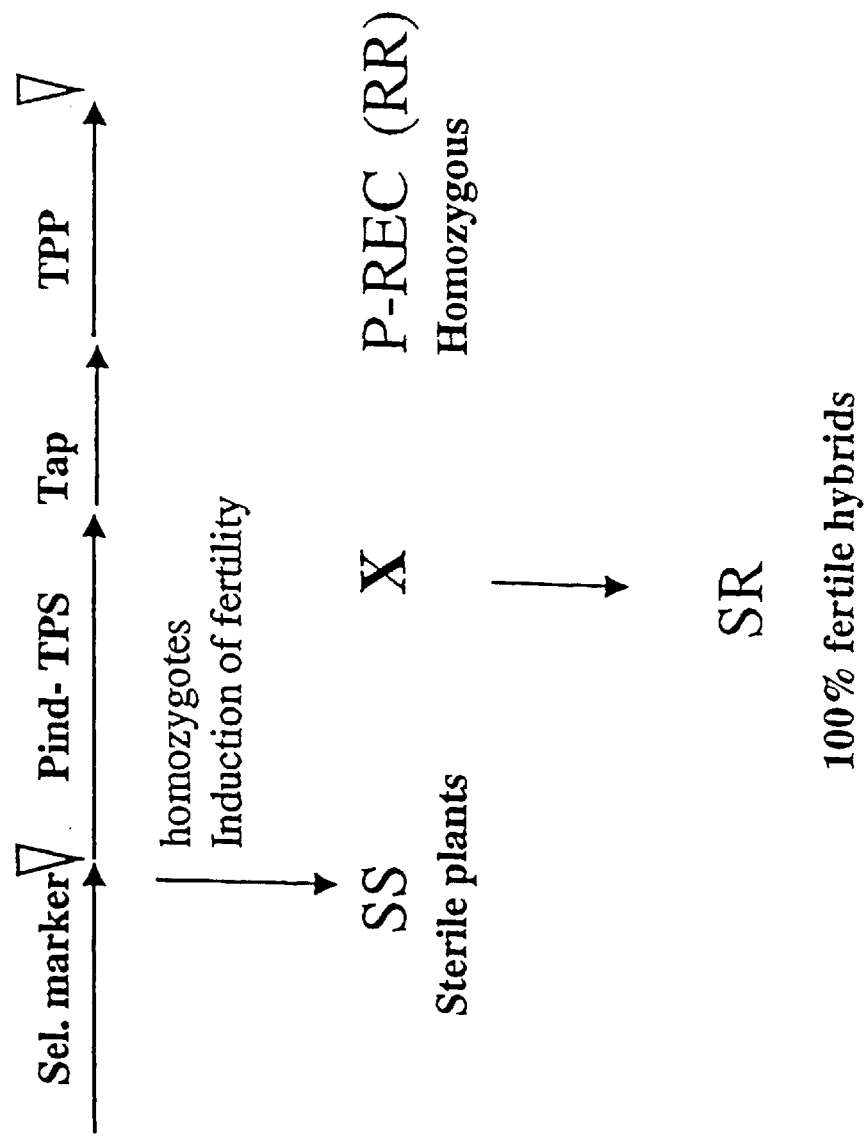
FIG. 2 Flow scheme of the production of fertile hybrids in a nuclear male sterility system based on the expression of TPP, restoration by the expression of TPS and site-specific recombination.
Figure 3:
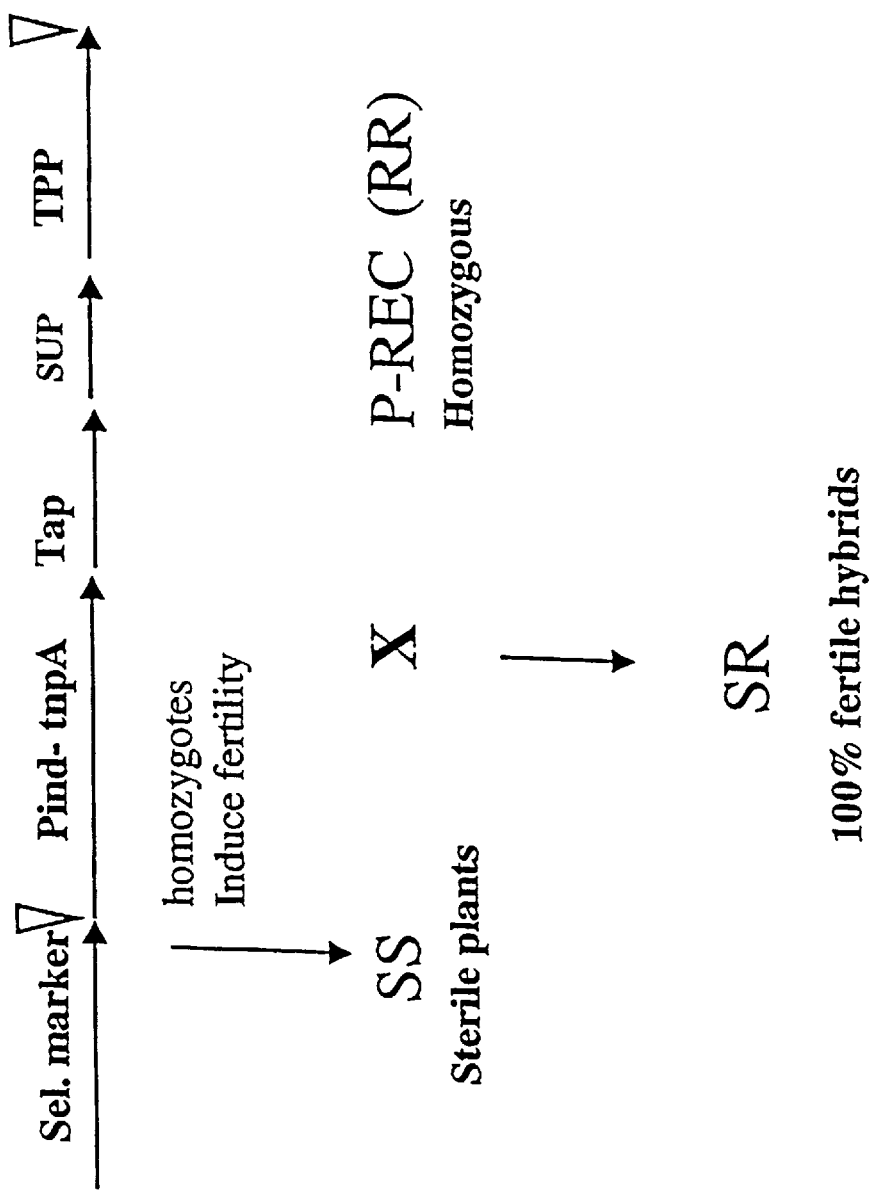
FIG. 3 Flow scheme of the production of fertile hybrids in a nuclear male sterility system based on the expression of TPP, restoration by the expression of a suppressor and site-specific recombination.
Figure 4:
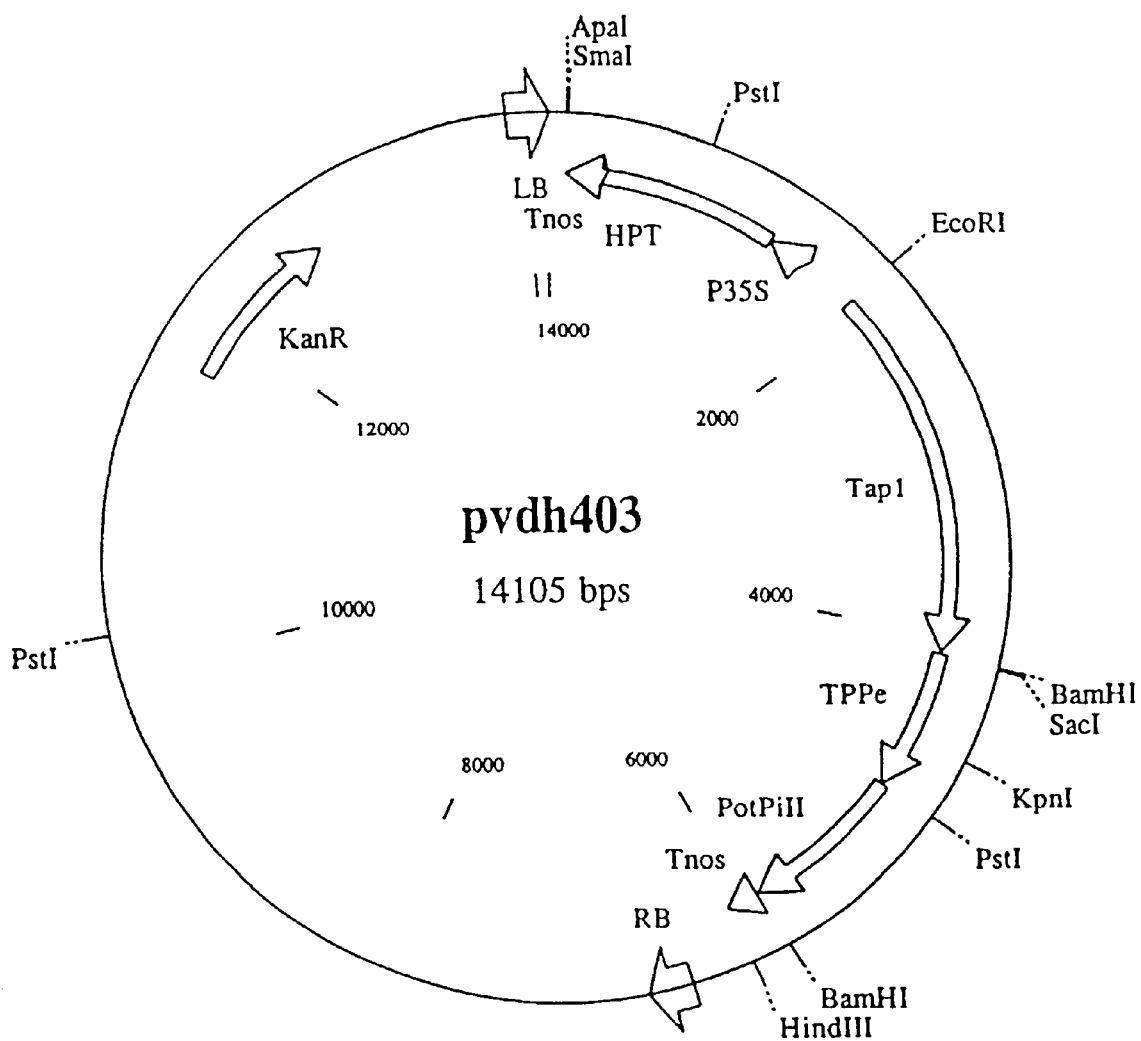
FIG. 4 Restriction site map of plasmid pvdh403, harboring the *E. coli* TPP gene under control of the Tap1 promoter and the constitutively expressed hpt selection marker.

Thus, fertility in the homozygous male sterile lines can be restored by treatment with the inducer, and these restored male fertile lines can be used to cross with themselves or, so that homozygosity is maintained, with the still-male sterile lines. In cases where a sterile line is preferable for marketing purposes, seeds resulting from the crosses of the restored fertile lines with the male sterile lines can be obtained and sold. In cases where the heterosis effect is sought and fertile hybrids should be produced, a similar approach with site-specific recombination, as described above in the simple system, can be used. Therefore, site-specific recombination sites should be inserted flanking the TPP gene, preferably but not necessarily also including the TPS coding sequence, and production of fertile hybrids can be obtained by crossing the homozygous male sterile line with a line capable of expressing the site-specific recombinase. A flow-scheme depicting the above-described method is shown in FIG. 2.

Another example of a method of counteracting the effect of TPP to restore fertility is the introduction of the DNA coding for a suppressor protein, said suppressor capable of suppressing the expression of TPP, while the expression of the suppressor is under the control of an inducible promoter. Such suppression can, for example, be accomplished by use of the tet-repressor system, where a specific binding site recognized by the suppressor is introduced near the RNA-polymerase binding site of the gene whose expression is to be suppressed. If the tet-repressor is present, the suppressor will bind to the specific sequence and, by steric hindrance, prevent the RNA polymerase from initiating transcription of the gene. The gene coding for the tet-repressor can be adjacent to the gene whose expression should be controlled, but this is not necessary.

When the gene for the repressor is placed under the control of an inducible promoter, the expression of the suppressor molecule, and thus the suppression of the TPP gene, can be induced by applying an external inducer. Then the TPP effect will not be established, and normal fertile plants will result. Maintenance of the homozygous male sterile line is then possible by crossing male sterile plants with these restored fertile plants.

For the production of fertile hybrids, the system with the site-specific recombination as described above can be used.

A third way to restore fertility by counteracting the TPP effect is to introduce an antisense TPP gene under the control of an inducible promoter next to the TPP gene. After induction with the corresponding inducer, the antisense TPP will bind to the mRNA produced by the sense TPP gene and thus will prohibit further translation and sterility effects of the TPP gene. The gene for the antisense TPP can be adjacent to the gene for the sense TPP, but this is not necessary.

Surprisingly, a fourth method to restore fertility is to apply solutions of gibberellic acid (GA) to the male sterile plants, either directly by spraying onto the flower buds or indirectly through watering. Apparently, the GA is capable of overcoming the inhibitory effect of the expressed TPP. The GA preferably is applied during the development of the flower buds because otherwise the effects of TPP expression could be irreversible.

The recombinant DNA constructs of the present invention can be constructed using recombinant DNA technology known to those skilled in the art. The recombinant gene constructs can be inserted into vectors specifically suited for transformation of plants and the expression of the gene product in the transformed cells. These vectors may be commercially available. Transformed cells (those containing the recombinant DNA inserted into the host cell's DNA) are separated from untransformed cells through the use of a selectable marker included as part of the introduced recombinant DNA.

As regards the applicability of the invention in different plant species, it has to be mentioned that one particular embodiment of the invention is merely illustrated with transgenic tobacco plants as an example, the actual applicability being in fact not limited to this plant species. Any plant species may be provided with a recombinant DNA sequence according to the invention.

Although some of the embodiments of the invention may not be practicable at present, e.g. because some plant species are as yet recalcitrant to genetic transformation, the practicing of the invention in such plant species is merely a matter of time and not a matter of principle, because the amenability to genetic transformation as such is of no relevance to the underlying embodiment of the invention.

Transformation of plant species is now routine for an impressive number of plant species, including both the Dicotyledoneae as well as the Monocotyledoneae. In principle, any transformation method may be used to introduce recombinant DNA according to the invention into a suitable ancestor cell, as long as the cells are capable of being regenerated into whole plants. Methods may suitably be selected from the calcium/polyethylene glycol method for protoplasts (Krens, F.A. et al., 1982, Nature 296, 72–74; Negrutiu I. et al., Jun. 1987, Plant Mol. Biol. 8, 363–373), electroporation of protoplasts (Shillito R. D. et al., 1985 Bio/Technol. 3, 1099–1102), microinjection into plant material (Crossway A. et al., 1986, Mol. Gen. Genet. 202, 179–185), (DNA- or RNA-coated) particle bombardment of various plant material (Klein T. M. et al., 1987, Nature 327, 70), infection with (non-integrative) viruses and the like. A preferred method according to the invention comprises Agrobacterium-mediated DNA transfer. Especially preferred is the use of the so-called binary vector technology, as disclosed in EP-A-0 120 516 and U.S. Pat. No. 4,940,83. Tomato transformation can be performed essentially as described by Van Roekel et al. (1993, Plant Cell Reports 12, 644–647). Sugarbeets are transformed with use of their guard cells, as has been described in PCT/GB 93/211837.

Generally, after transformation, plant cells or cell groupings are selected for the presence of one or more markers that are encoded by plant-expressible genes co-transferred with the nucleic acid sequence encoding the protein according to the invention, whereafter the transformed material is regenerated into a whole plant.

Although considered somewhat more recalcitrant towards genetic transformation, monocotyledonous plants are amenable to transformation, and fertile transgenic plants can be regenerated from transformed cells or embryos or other plant material. Presently, preferred methods for transformation of monocots are microprojectile bombardment of embryos, explants, or suspension cells, direct DNA uptake or electroporation (Shimamoto, et al., 1989, Nature 338, 274–276), and whiskers technology. More specifically, transgenic maize has been transformed using a silicon carbide fibre-mediated transformation technique (whiskers) as follows: sterile, autoclaved whisker suspensions in CMS medium were mixed with a cell suspension and the DNA and vortexted. Next, transgenic calli were obtained on a selective medium (described, e.g., in WO 97/04116). Transgenic maize plants have also been obtained by introducing the Streptomyces hygroscopicus bar-gene, which encodes phosphinothricin acetyltransferase (an enzyme which inactivates the herbicide phosphinothricin), into embryogenic cells of a maize suspension culture by microprojectile bombardment (Gordon-Kamm, 1990, Plant Cell 2, 603–618). The introduction of genetic material into aleurone protoplasts of other monocot crops, such as wheat and barley, has been reported (Lee, 1989, Plant Mol. Biol. 13, 21–30). Wheat plants have been regenerated from embryogenic suspension culture by selecting only the aged compact and nodular embryogenic callus tissues for the establishment of the embryogenic suspension cultures (Vasil, 1990, Bio/Technol. 8, 429–434). The combination with transformation systems for these crops enables the application of the present invention to monocots.

Monocotyledonous plants, including commercially important crops such as rice and corn, are also amenable to DNA transfer by Agrobacterium strains (WO 94/00977; EP 0 159 418 BI; Gould J. et al. 1991, Plant Physiol. 95, 426–434).

Following DNA transfer and regeneration, putatively transformed plants may be evaluated, for instance using Southern analysis, for the presence of the recombinant DNA according to the invention, copy number and/or genomic organization. In addition, or alternatively, expression levels of the newly introduced DNA may be undertaken, using Northern and/or Western analysis, techniques well known to persons having ordinary skill in the art. After the initial analysis, which is optional, transformed plants showing the desired copy number and expression level of the newly introduced recombinant DNA according to the invention may be tested for their male sterility or restoration to fertility. Alternatively, the selected plants may be subjected to another round of transformation, for instance to introduce further genes, such as the TPS gene or the suppressor gene.

To obtain transgenic plants capable of constitutively expressing more than one chimeric gene, a number of alternatives are available including the following:

A. The use of DNA, e.g. a T-DNA on a binary plasmid, with a number of modified genes physically coupled to a selectable marker gene. The advantage of this method is that the chimeric genes are physically coupled and therefore migrate as a single Mendelian locus.

B. Cross-pollination of transgenic plants, each already capable of expressing one or more chimeric genes, preferably coupled to a selectable marker gene, with pollen from a transgenic plant that contains one or more chimeric genes coupled to another selectable marker. Afterwards, the seed, which is obtained by this crossing, may be selected on the basis of the presence of the two selectable markers or on the basis of the presence of the chimeric genes themselves. The plants obtained from the selected seeds can afterwards be used for further crossing. In principle, the chimeric genes are not on a single locus, and the genes may, therefore, segregate as independent loci.

C. The use of a number of a plurality chimeric DNA molecules, e.g. plasmids, each having one or more chimeric genes and a selectable marker. If the frequency of co-transformation is high, then selection on the basis of only one marker is sufficient. In other cases, the selection on the basis of more than one marker is preferred.

D. Consecutive transformation of transgenic plants already containing a first, second, etc. chimeric gene with new chimeric DNA, optionally comprising a selectable marker gene. As in method B, the chimeric genes are, in principle, not on a single locus, and the chimeric genes may, therefore, segregate as independent loci.

E. Combinations of the above mentioned strategies.

After having obtained the male sterile parent line, it should be crossed with another parent line (which has to be male fertile) to obtain the hybrids. If the goal is to provide male sterile hybrids, the sterile parent line should be homozygous and the fertile parent line may be any line, including wild-type plants. This method is ideal for crops that do not have to produce seeds, such as lettuce, cauliflower, carrot, etc.

If the goal is to provide fertile hybrids, the effects of TPP in the male sterile line should be overcome. This can be done in several ways, only some of which will be mentioned here. The invention is not limited to these examples, and a person skilled in the art can easily find other ways of achieving the same goal.

A first method to obtain fertile hybrids is to cross the male sterile line with a line expressing a site-specific recombinase. For this purpose, the male sterile line should include site-specific recombination sites flanking the gene encoding TPP. Upon crossing the dominant male sterile line with a parent line that expresses the recombinase, the TPP gene will be excised, and the offspring will be fertile.

A further method for obtaining fertile hybrids is to cross the dominant male sterile line with a parent line that is transformed with and overexpresses the gene encoding TPS. TPS is an enzyme that is capable of neutralizing the effects of TPP, and plants that express both TPP and TPS are male fertile. Preferably, the TPS is also expressed specifically in the male reproductive system.

Another method for obtaining fertile hybrids is crossing the dominant male sterile line with a parent line that is transformed with an antisense TPP gene. Upon crossing, the mRNA produced by the antisense TPP gene will align with the mRNA from the sense TPP gene and thus prevent translation of the mRNA. Hence, the TPP enzyme will not be formed, and the resulting hybrids are fertile.

An additional method for obtaining fertile hybrids is the use of a suppressor system. In this method, the expression of TPP in the dominant male sterile line may be suppressed by a suppressor that binds to the DNA and thus prevents transcription of the TPP gene. The parent line with which the male sterile line is crossed should be capable of expressing the suppressor.

A final method to obtain fertile hybrids is to treat a part of the male sterile plants with gibberellic acid (GA) during the development of the flower buds. The male sterile plants will then become fertile and will be capable of crossing with female fertile plants.

The invention is extremely useful in plants which are known to generate heterosis upon the formation of hybrids and plants for which prevention of breeding with farm-saved seed is sought. Such plants are sorghum, Brassica, rice, wheat, rye, corn, tomato, pepper, cucumber, melon, ornamentals and field crops such as carrot, onion, leak, sunflower, grasses, lettuce and sugarbeet. The person skilled in the art will recognize that this list is not complete and that also other plants can benefit from this invention.

The following examples are further provided for illustrative purposes only and are in no way intended to limit the scope of the present invention.

EXPERIMENTAL PART

Standard methods for the isolation, manipulation and amplification of DNA, as well as suitable vectors for replication of recombinant DNA, suitable bacterium strains, selection markers, media and the like are described for instance in the handbook of Sambrook et al. (Sambrook, J., Fritsch, E. F., and Maniatis, T. (1989) Molecular Cloning: A Laboratory Manual. Cold Spring Harbor Laboratory Press, Cold Spring Harbor, N.Y.).

EXAMPLE 1

Transformation of tobacco, lettuce and Arabidopsis

Transformation of lettuce, Lattuca sativa cv. Evola, was performed according to Curtis et al. (1994) J. Exp. Bot. 45, 1441. Transformation of *Arabidopsis thaliana* was carried out either by the method described by Clarke et al. (1992) Plant. Mol. Biol. Rep. 10, 178 or by the method described by Valvekens et al. (1988) Proc. Natl. Acad. Sci. USA, 85, 5536.

In vitro shoots of Nicotiana tabacum Samsun NN were grown on basic MS20 medium (Murashige and Skoog basic salts and vitamins included with 20 grams sucrose without hormones) for 4 weeks until they developed full-grown leaves. At this stage, leaves were used for transformation with Agrobacterium strains, which were stored at -80° C in a 35% glycerol stock. Before use, the Agrobacterium were grown on solid LLC medium with RTK for 3 days at 29° C. The strains were put in 20 ml liquid LLC medium with RTK and grown overnight while shaking at 300 RPM. The next day the strains were fully grown (O.D >>1.5) and ready for use. Strains containing the plasmid pVDH403 (Tap1-TPP) were denominated Hat 1403, and strains containing the plasmid pVDH417 (Tap1-TPS) were denominated Hat 1417.

Full-grown tobacco leaves were sterile cut in small parts from 1 by 1 cm. These explants were put for 5 to 10 minutes into the overnight grown Agrobacterium culture to start the cocultivation. The explants were taken out of the suspension and put on sterile filterpaper to reduce the concentration of bacteria. The explants were put upside down on cocultivation medium for 2 to 3 days at 20° C in the dark. After that, the explants were put in sterile water to remove the bacteria. The explants were then put on sterile filter paper to remove excess water. The explants were transferred to counterselection medium to kill the bacteria completely for 3 days at 22° C and 16/24 hours light.

Explants were transferred to regeneration medium to produce transgenic shoots in about 4 to 6 weeks at 22° C and 16/24 hours light. To ensure good regeneration, the explants were placed upside down on the regeneration medium. When the transgenic shoots were about I cm, they were transferred to rooting medium. If the shoots were able to produce shoot meristems after 2 to 4 weeks on rooting medium with 100 mg/l kanamycin, the rooting medium was refreshed. After rooting the independent transgenic shoots, the plants were transferred to the soil in the greenhouse. After 6 to 10 weeks in the greenhouse, the plants started to flower. The composition of the media was as follows:

| MS20 medium (in vitro shoot proliferation) | |
|---|---|
| MS salts and vitamins (Murashige and Skoog) | 4.61 g/l |
| Sucrose | 20.0 g/l |
| MES (Morpholino Ethane Sulfonic Acid) | 0.3 g/l |
| Agar (Purified, Sigma) | 8.0 g/l |
| PH | 5.8 |
| Autoclave (20 min. 121° C.). | |
| Cocultivation medium | |
| MS salts and vitamins | 4.61 g/l |
| Sucrose | 20.0 g/l |
| MES | 0.3 g/l |
| Agar | 8.0 g/l |
| PH | 5.8 |
| Autoclave (20 min. 121° C.) | |
| Counterselection medium | |
| MS salts and vitamins (Murashige and Skoog) | 4.61 g/l |
| Sucrose | 20.0 g/l |
| MES (Morpholino Ethane Sulfonic Acid) | 0.3 g/l |
| BAP (6-Benzylaminopurine) | 1.0 g/l |
| Cx (Cefotaxime) (Filtersterile) | 100 mg/l |
| PH | 5.8 |
| Autoclave (20 min. 121° C.). | |
| Regeneration medium | |
| MS salts and vitamins | 4.61 g/l |
| Sucrose | 20.0 g/l |
| MES | 0.3 g/l |
| BAP | 1.0 g/l |
| Cx (Cefotaxime) (Filtersterile) | 100 mg/l |
| Km (Kanamycine) (Filtersterile) | 100 mg/l |
| PH | 5.8 |
| Autoclave (20 min. 121° C.). | |
| Rooting medium | |
| MS salts and vitamins | 4.61 g/l |
| Sucrose | 20.0 g/l |
| MES | 0.3 g/l |
| Cx (Cefotaxime) (Filtersterile) | 100 mg/l |
| Km (Kanamycine) (Filtersterile) | 100 mg/l |
| Agar | 8.0 g/l |
| PH | 5.8 |
| Autoclave (20 min. 121° C.). | |
| LLC medium | |
| Bacto-Tryptone | 10.0 g/l |
| Yeast extract | 5.0 g/l |
| NaCl | 5.0 g/l |
| Tris-HCl (1.0 Molair, pH 7.5) | 1.0 ml/l |
| Autoclave (20 min. 121° C.) | |
| PH | 7.0 |
| Solid LLC contains also Bacto-Agar | 15.0 g/l |
| Antibiotics (RTK) (Filtersterile) | |
| Solid LLC: Rifampycine | 100 mg/l |
| Tetracycline | 5 mg/l |
| Kanamycine | 50 mg/l |
| Liquid LLC: Rifampycine | 40 mg/l |
| Tetracycline | 2 mg/l |
| Kanamycine | 50 mg/l |

EXAMPLE 2

Construction of plasmids pVDH403, pVDH417, pVDH512 (=pMOG1301) and pVDH517

Figure 5:
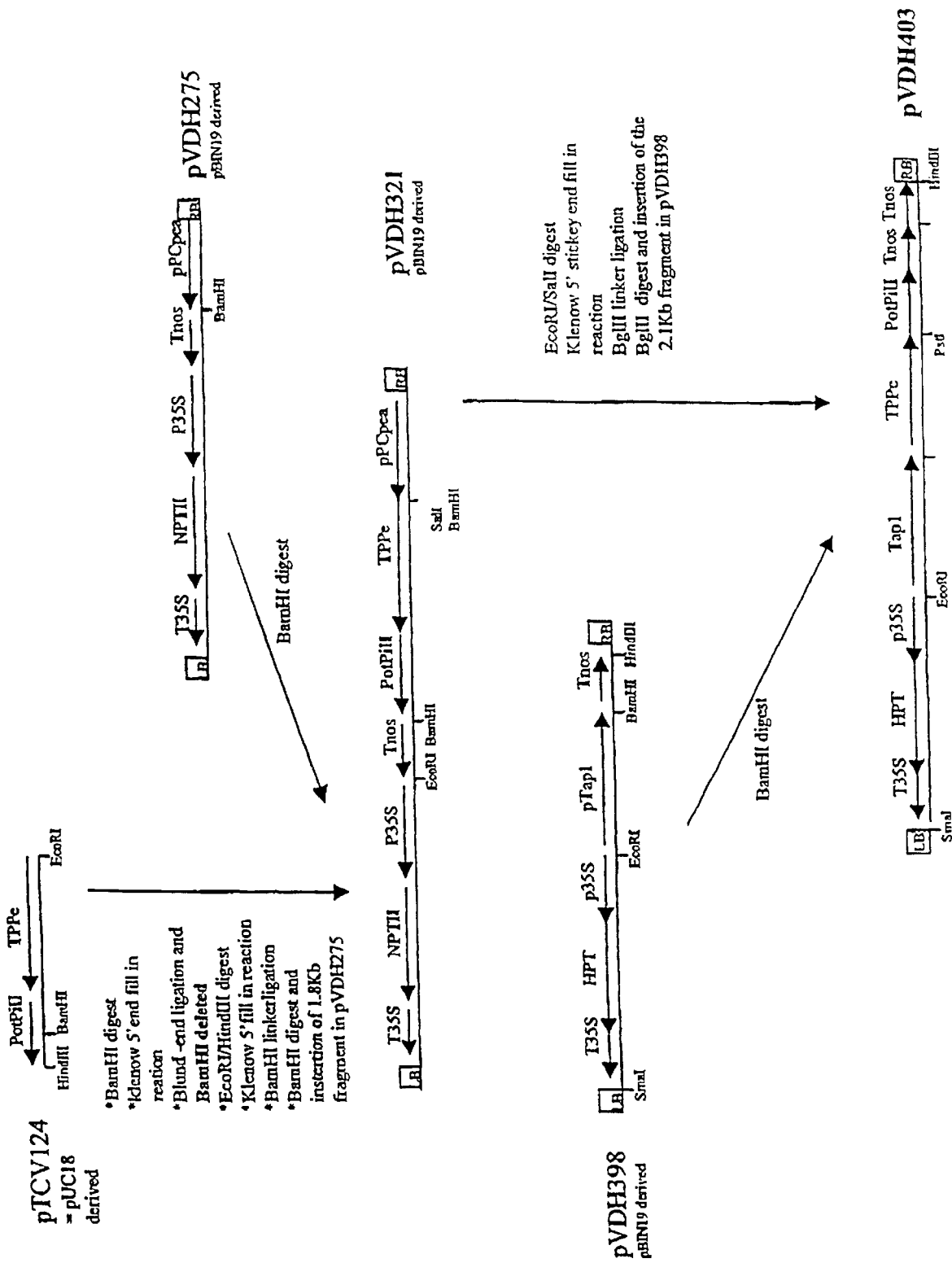
FIG. 5 Cloning scheme for the construction of pVDH403.
Figure 6:
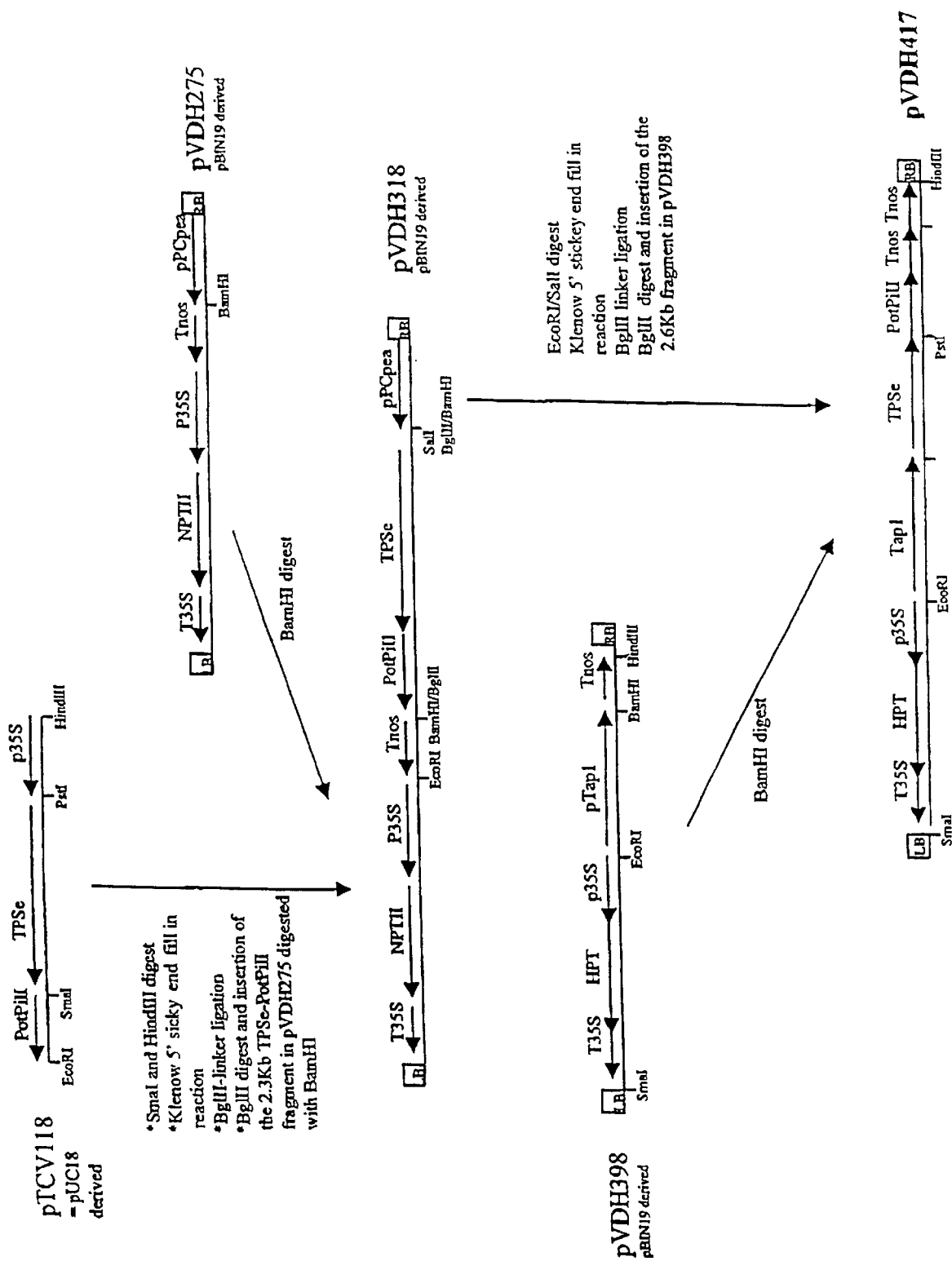
FIG. 6 Cloning scheme for the construction of pVDH417.

The construction scheme of pVDH403 and pVDH417 is depicted in FIG. 5 and FIG. 6, respectively. The construction of the plasmids pVDH321 and pVDH318, which are intermediates in this scheme, has been described in PCTIEP97/02497. pVDH398 contains the Tap1 promoter as described by Nacken et al., 1991, Mol. Gen. Genet. 229, 129–136.

For the construction of pVDH512 (harboring the trehalose phophate hydrolase under control of the plastocyanin promoter, PC-TreC =pMOG1301) two oligonucleotide primers were synthesized, Tre-TreC-46 (Forward primer containing BamHI site) and Tre-TreC47 (Reverse primer containing BamHI site), complementary to the *E. coli* Tre C gene as described by Rimmele, M., and Boos, W. 1994, Trehalose-6-phosphate hydrolase of *Escherichia coli*. J. Bact. 176:5654–5664. Tre-TreC-46 5' CTCGGATCCG-TAATGACTCATCTTCCCCAC 3'Tre-TreC-47 5' CTCG-GATCCGATTTACTTCTGTAACCACC 3'

Similar to the construction of a PC TPP expression construct (WO 97/42326), binary vectors were generated harboring the pea plastocyanin promoter linked to the *E. coli* TreC gene.

Similar to the construction of pVDH417, a plant binary vector was constructed harboring the *E. coli* TPS gene under control of a tapetum- specific promoter with a kanamycin plant selectable marker on the T-DNA. This construct was denominated pVDH517.

EXAMPLE 3

Scoring of seed production

Figure 7:
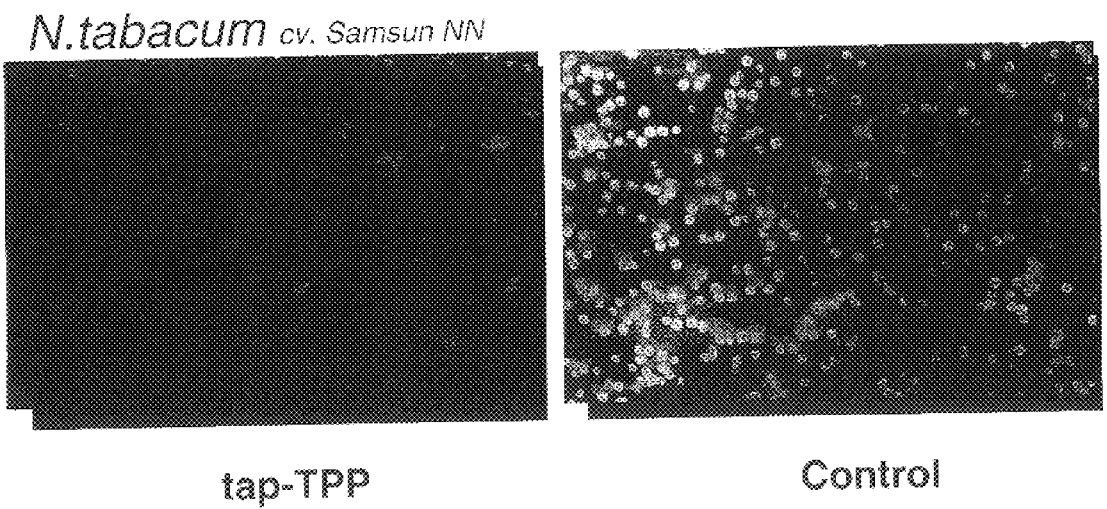
FIG. 7 Pollen vitality fluorescence staining of pollen derived from tap-TPP transformed and wild-type Samsun NN tobacco plants.

There were 20 independent transformants produced with Hat 1403 and 5 with Hat 1417. These plants were transferred to the greenhouse, and, at flowerstage, the vitality of the pollen was determined with FDA (flouresceine diacetate) 0.01% (FIG. 7). Sterile plants were backcrossed with non-transformed Samsum NN pollen to confirm the transformants were only male sterile and not female sterile. Flowering seed production was scored. Plants with a very low selfing seed were also harvested, and the seeds were sown again to determine if the S1 seeds were viable. The scorings are listed in Table 1. To analyse the correlation between the presence of the TPP gene and male sterility, tap-TPP transgenic tobacco plant lines were backcrossed to wild-type plants according to the scheme of Table 2. The presence of the TPP gene in offspring was assessed using PCR technology and phenotypic scoring (Table 3).

TABLE 1

Phenotype of *N. tabacum* Samsun NN containing Tap-TPP (1403) or Tap-TPS (1417); − = 0 seeds/fruit, +/− = 1–5 seeds/fruit, + = 10–100 seeds/fruit, ++ = normal seed set in some fruits +++ = normal seed set

| Plant # | Pollen viability (%) | Flower morphology | seeds (selfed) | F1 seeds (Wt) |
|---|---|---|---|---|
| 1403-01 | 5 | Wt | ++ | +++ |
| 1403-02 | <1 | Wt | ++ | ND |
| 1403-03 | 30 | Wt | +++ | +++ |
| 1403-04 | <1 | Wt | ++ | +++ |
| 1403-05 | <1 | Wt | ++ | ND |
| 1403-06 | 0 | Wt | +/− | ND |
| 1403-07 | 0 | Wt | +/− | ND |
| 1403-08 | <1 | Wt | ++ | +++ |
| 1403-09 | 0 | Wt | ++ | +++ |
| 1403-10 | <1 | Wt | − | +++ |
| 1403-11 | 0 | Wt | +/− | ND |
| 1403-12 | 75 | Wt | +++ | ND |
| 1403-13 | 0 | Wt | − | ND |
| 1403-14 | 75 | Wt | +++ | ND |
| 1403-15 | <1 | Wt | − | +++ |
| 1403-16 | 0 | abb. anthers | − | ND |
| 1403-17 | 0 | Wt | +/− | ND |
| 1403-18 | 0 | Wt | ++ | ND |
| 1403-19 | 5 | Wt | ++ | +++ |
| 1403-20 | 0 | abb. anthers | +/− | ND |

TABLE 1-continued

Phenotype of *N. tabacum* Samsun NN containing Tap-TPP (1403) or Tap-TPS (1417); − = 0 seeds/fruit, +/− = 1–5 seeds/fruit, + = 10–100 seeds/fruit, ++ = normal seed set in some fruits +++ = normal seed set

| Plant # | Pollen viability (%) | Flower morphology | seeds (selfed) | F1 seeds (Wt) |
|---|---|---|---|---|
| Samsun wt | 75 | Wt | +++ | ND |
| 1417-08 | >10 | Wt | +++ | ND |
| 1417-12 | >10 | Wt | +++ | ND |
| 1417-13 | >10 | Wt | +++ | ND |
| 1417-19 | >10 | Wt | +++ | ND |
| 1417-20 | >10 | Wt | +++ | ND |

TABLE 2

Numbering of backcross of Tap-TPP with wild-type tobacco plants Tap-TPP transgenic tobacco plant lines

|  | 1403-20 | 1403-10 | 1403-6 | 1403-7 | 1403-17 |
|---|---|---|---|---|---|
| wild-type | F | B | H | D | J |

TABLE 3

PCR-data of offspring and phenotypical analysis.

| Tap-TPP | Cross | Plant no. | PCR | Sterility |
|---|---|---|---|---|
| 1403-20 | F | 1 | + | S |
|  | F | 2 | − | F |
|  | F | 3 | + | S |
|  | F | 4 | − | F |
|  | F | 5 | + | S |
|  | F | 6 | + | S |
| 1403-10 | B | 1 | + | S |
|  | B | 2 | − | F |
|  | B | 3 | − | F |
|  | B | 4 | + | S |
|  | B | 5 | + | S |
|  | B | 6 | − | F |
| 1403-6 | H | 1 | − | F |
|  | H | 2 | + | S |
|  | H | 3 | + | S |
|  | H | 4 | + | ND |
|  | H | 5 | + | ND |
|  | H | 6 | + | ND |
| 1403-7 | D | 1 | + | S |
|  | D | 2 | + | S |
|  | D | 3 | + | S |
|  | D | 4 | + | S |
|  | D | 5 | + | S |
|  | D | 6 | + | S |
| 1403-17 | J | 1 | − | F |
|  | J | 2 | − | F |
|  | J | 3 | − | F |
|  | J | 4 | + | S |
|  | J | 5 | + | S |
|  | J | 6 | + | S |

ND: Not determined; S: Plant is sterile; F: Plant is fertile

EXAMPLE 4

Generation of sterile tobacco plants by expressing PC-TreC

Transgenic tobacco plants were generated expressing a bacterially-derived trehalose-6-phosphate hydrolase (Rimmele and Boos) under control of the green-specific plastocyanin promoter (pMOG1301). Similar to tobacco plants expressing the *E. coli*-derived TPP gene (WO 97/42326), plants expressing TreC developed large leaves having bleached interveinal tissue. After formation of flowerbuds; premature abscission of these buds occurred, resulting in fully sterile plants.

EXAMPLE 5

Generation of sterile lettuce plants by expressing Tap-TPP

Transgenic lettuce plants were generated expressing the *E. coli*TPP gene under control of the tapetum-specific promoter (pVDH403). 33 of 126 independent primary transformants were proven to be male sterile. A backcross of a selection of the male sterile plants to wild-type plants (Table 4) and subsequent analysis of the offspring by correlating the sterility with the presence of the TPP gene indicated a 100% correlation.

TABLE 4

Numbering of backcross of Tap-TPP with wild-type lettuce plants and PCR-data of offspring of backcross.

| Female parent | X | Male parent | Backcross |
|---|---|---|---|
| Tap-TPP |  |  |  |
| 3A-01 | X | Wild-type |  |
| 4E-02 | X | Wild-type |  |

| Plant code offspring | PCR TPP/PCR HPT | Phenotype |
|---|---|---|
| 3A-01-01 | −/− | F |
| 3A-01-02 | −/− | F |
| 3A-01-03 | −/− | F |
| 3A-01-04 | +/+ | S |
| 3A-01-05 | +/+ | S |
| 4E-02-01 | +/+ | S |
| 4E-02-02 | +/+ | S |
| 4E-02-03 | −/− | F |
| 4E-02-04 | −/− | F |

F: Fertile
S: Sterile

EXAMPLE 6

Restoration of fertility in tobacco Tap-TPP plants by retransformation with pVDH417 (Tap-TPS)

Figure 8:
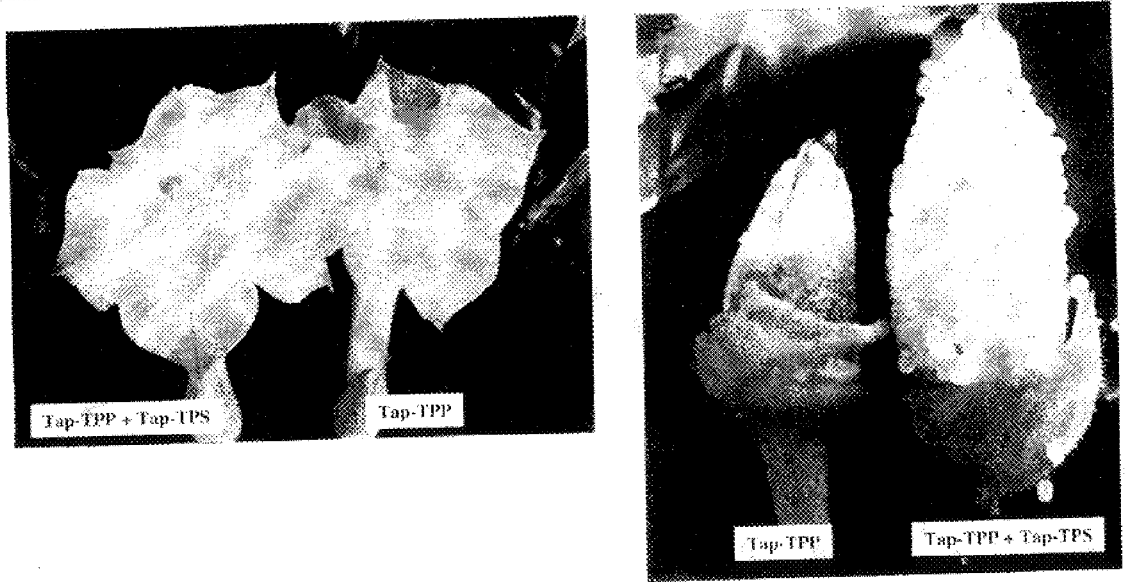
FIG. 8 Restoration of fertility of tap-TPP tobacco Samsun NN plants after retransformation with tap-TPS. Left panel shows development of pollen on the anthers in the flower. Right panel shows seed setting of the respective transgenic plant lines.

Tobacco plants transgenic for Tap-TPP (pVDH403, T-DNA harbors a hygromycin plant selectable marker) and displaying a male sterile phenotype were retransformed with Tap-TPS (pVDH417, T-DNA harbors a kanamycin plant selectable marker), and the retransformants were analysed on fertility (Table 5). Four of the five male sterile lines selected for retransformation were proven to regain their fertility when expressing Tap-TPS and Tap-TPP simultaneously as shown in FIG. 8.

TABLE 5

Tap-TPS (pVDH517) transformed to male sterile Tap-TPP (pVDH403) tobacco plants.

| Plant no. | 1403-20 A1 | 1403-10 B1 | 1403-6 C1 | 1403-7 D1 | 1403-17 O1 |
|---|---|---|---|---|---|
| 1 | F | F | * | S | F |
| 2 | F | F | F | S | F |
| 3 | F | F | F | S | * |
| 4 | F | F | F? | * | * |
| 5 | F | F | F | S | F |
| 6 | F | * | * | S | F |
| 7 | F | S | F | S | F |
| 8 | F | F | F | ND | F |

TABLE 5-continued

Tap-TPS (pVDH517) transformed to male sterile Tap-TPP
(pVDH403) tobacco plants.

| Plant no. | 1403-20 A1 | 1403-10 B1 | 1403-6 C1 | 1403-7 D1 | 1403-17 O1 |
|---|---|---|---|---|---|
| 9  | F  | F  | F | S  | ND |
| 10 | F  | F  | F | ND | F  |
| 11 | F  | S  | F | S  | F  |
| 12 | F  | S  | F | *  | F  |
| 13 | F  | F  | F | *  | F  |
| 14 | ND | F  | F | ND | F  |
| 15 | ND | ND | F | S  | F  |
| 16 | ND | ND | F | ND | F  |
| 17 | ND | ND | F | ND | F  |
| 18 | ND | ND | F | ND | S  |
| 19 | ND | ND | F | ND | F  |
| 20 | ND | ND | F | ND | *  |

ND: Not determined
*: Not flowering yet
S: Plant is sterile
F: Plant is fertile
F?: Plant produces low amount of seeds In addition, 32 tobacco plants transformed with Tap-TPS only were generated. All plants were fertile, did set seed, and did not display a specific phenotype different from that of wild-type plants.

EXAMPLE 7

Restoration of fertility in tobacco Tap-TPP plants by treatment with gibberellic acid (GA)

Male sterile tobacco plants transgenic for Tap-TPP (pVDH403) were treated with a Berelex solution (Abbott), containing GA4 and GA7, diluted to a GA concentration of 20 mg/I, which was sprayed on developing flowerbuds using a conventional plant-spray device. Plants were sprayed every two days from the start of flowerbud formation until pollination. Using this treatment, normal fertile pollen were produced on the Tap-TPP plant lines, resulting in self-fertilisation and seed-setting (FIG. 9). Comparable to Example 6, four of the five male sterile lines selected for GA treatment were proven to regain their fertility when sprayed with the Berelex solution (Table 6 ).

TABLE 6

Restoration of fertility in Tap-TPP
tobacco plants by GA-treatment.

Plant-lines transformed with Tap-TPP (pVDH403)

| Plant no. | 403-20 A1 | 403-10 B1 | 403-6 C1 | 403-7 D1 | 403-17 O1 |
|---|---|---|---|---|---|
| 1 | S | F | S | S | F |
| 2 | S | S | S | S | S |
| 3 | F | F | S | * | F |
| 4 | F | S | F | S | S |
| 5 | S | S | F | S | S |

*: Not flowering yet
S: Plant is sterile
F: Plant is fertile
F?: Plant produces low amount of seeds
Shaded and underlined scores have been treated with GA, other scores have not been treated.

EXAMPLE 8

Restoration of fertility of tobacco PC-TreC transgenic plants by treatment with gibberellic acid (GA)

Male sterile tobacco plants transgenic for PC-TreC (pMOG1301) were treated with a Berelex solution (Abbott), containing GA4 and GA7, diluted to a GA concentration of 20 mg/I, which was sprayed on developing flowerbuds using a conventional plant-spray device. Plants were sprayed every two days from the start of flowerbud formation until pollination. Using this treatment, premature abscission of flowerbuds was prevented, and flowers producing fertile pollen were able to self-fertilise, resulting in seed- setting.

EXAMPLE 9

Generation of sterile tobacco plants by expressing PC-TPP

Transgenic tobacco plants were generated expressing the trehalose-6-phosphate phosphatase gene (WO 97/42326) under control of the green-specific plastocyanin promoter (pVDH321). Plants expressing TPP developed large leaves having bleached interveinal tissue. After formation of flowerbuds, premature abscission of these buds occurred, resulting in fully sterile plants.

EXAMPLE 10

Restoration of fertility of tobacco PC-TPP transgenic plants by treatment with gibberellic acid (GA)

Male sterile tobacco plants transgenic for PC-TPP (pVDH32 1) were treated with a Berelex solution (Abbott), containing GA4 and GA7, diluted to a GA concentration of 20 mg/l, which was sprayed on developing flowerbuds using a conventional plant-spray device. Plants were sprayed every two days from the start of flowerbud formation until pollination. Using this treatment, premature abscission of flowerbuds was prevented, and flowers producing fertile pollen were able to self-fertilise, resulting in seed-setting.

EXAMPLE 11

Generation of sterile Arabidopsis plants by expressing PC-TPP

Transgenic Arabidopsis plants were generated expressing the trehalose-6-phosphate phosphatase gene (WO97/42326) under control of the green-specific plastocyanin promoter (pVDH321). Plants expressing TPP developed large leaves having bleached interveinal tissue. Plants expressing the TPP gene do not form inflorescences and are unable to produce seeds.

What is claimed is:

1. A recombinant DNA comprising a tapetum-, pollen-, and/or anther-specific promoter operably linked to a structural gene encoding trehalose phosphate phosphatase (TPP), wherein said TPP is from *E. coli* or yeast.

2. A recombinant DNA according to claim 1, wherein said promoter is the Tap1 promoter or the MFS 14 promoter.

3. A recombinant DNA according to claim 1, wherein said promoter is inducible.

4. A recombinant DNA according to claim 1, further comprising a selectable marker.

5. A recombinant DNA according to claim 4, wherein said selectable marker confers tolerance to a herbicide.

6. A recombinant DNA according to claim 5, wherein said selectable marker confers tolerance to N-phosphomethylglycine.

7. A vector comprising the recombinant DNA according to claim 1.

8. An Agrobacterium strain comprising the vector according to claim 7.

9. A plant transformed with the vector according to claim 7.

10. A plant transformed with the Agrobacterium strain of claim 8.

11. A male sterile plant characterized in that it comprises a recombinant DNA according to claim 1.

12. A method for making a plant male sterile comprising introducing a recombinant DNA according to claim 1, into a plant cell and regenerating a plant from said cell.

13. A method according to claim 12, wherein said plant is a dicotyledon.

14. A male sterile plant characterized in that it is made according to the method of claim 12.

* * * * *

```
                              SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: oligonucleotide primer Tre-TreC-46

<400> SEQUENCE: 1
ctcggatccg taatgactca tcttccccac                                         30

<210> SEQ ID NO 2
<211> LENGTH: 29
<212> TYPE: DNA
<213> ORGANISM: Artificial Sequence
<220> FEATURE:
<223> OTHER INFORMATION: oligonucleotide primer Tre-TreC-47

<400> SEQUENCE: 2
ctcggatccg atttacttct gtaaccacc                                          29
```